United States Patent [19]
Detweiler et al.

[11] Patent Number: 6,022,828
[45] Date of Patent: Feb. 8, 2000

[54] XANTHOMONAS CAMPESTRIS AS BIOLOGICAL CONTROL OF *POA TRIVIALIS*

[75] Inventors: Alvin Ronald Detweiler, Haslett; Joseph M. Vargas, Jr., East Lansing; Nancy M. Dykema, Holt; Jon F. Powell, Lansing, all of Mich.

[73] Assignee: Board of Trustees operating Michigan State University, East Lansing, Mich.

[21] Appl. No.: 09/103,119

[22] Filed: Jun. 23, 1998

[51] Int. Cl.[7] .............................. A01N 63/00; C12N 1/00; C12N 1/12
[52] U.S. Cl. ...................... 504/117; 424/93.1; 435/243; 435/252.1; 435/910; 435/911
[58] Field of Search ......................... 424/93.1; 435/243, 435/252.1, 911, 910; 504/117

[56] References Cited

U.S. PATENT DOCUMENTS 5,077,045  12/1991  Roberts ...................................... 424/93
5,192,541   3/1993  Savage et al. ......................... 424/93 D

OTHER PUBLICATIONS

Roberts, D.L., et al Plant Disease 65:1014–1015 (1981).
Roberts, K.D., et al, Plant Disease 66:804–806 (1982).
Roberts, D.L. et al, Scanning Electron Microscopy IV, 1719–1722 (1983).
Roberts, D.L., Phytopathology 73:810 (1984).
Roberts, D.L., Phytopathology 74:813 (1984).
Roberts, D.L., Phytopathology 75:1289 (1985).
Elgi, T. et al., Phytopath Z. 82:111–121 (1975).
Wilkins, P.W., et al., Plant Path 26:99 (1977).
DeCleene, M., et al., Parasitica 37(1) 29–34 (1981).
Leyns, F., et al., Parasitica 37:131–133 (1981).
VanDen Mooter, M., et al., Med FAc Landbouww Rijksuniv Gent 46/3, 787–792 (1981).
Van Den Mooter, M., et al Parasitica 37(1):23–28 (1981).
Proc. Fifth Int. Conf. Path Bact, Calif. 332–333 (1981).
Egli, T., et al., Phytopath Z. 104, 138–150 (1982).
Leyns, et al., Med. Fac. Landbouww Rijksuniv Gent. 47/3 1079–1081 (1982).

*Primary Examiner*—S. Mark Clardy
*Assistant Examiner*—Alton Pryor
*Attorney, Agent, or Firm*—Ian C. McLeod

[57] ABSTRACT

A method for controlling *Poa trivialis* using a bacterium which is a *Xanthomonas campestris* pathovar which produces a wilt in the weed grass is described. In particular, the use of a *Xanthomonas campestris* which infects the *Poa trivialis* types to suppress or kill this weed grass is described. The method allows non-weedy grasses to develop without interference from *Poa trivialis* to improve lawns, golf courses and the like.

12 Claims, No Drawings

XANTHOMONAS CAMPESTRIS AS BIOLOGICAL CONTROL OF POA TRIVIALIS

CROSS-REFERENCE TO RELATED APPLICATION

A Provisional Application was filed on Jul. 2, 1997 as Ser. No. 60/051,590.

BACKGROUND OF THE INVENTION

(1) Summary of the Invention

The present invention relates to a method for controlling *Poa trivialis* by infecting it with a *Xanthomonas campestris* pathovar which does not infect non-weed grasses. In particular, the present invention relates to the use of *Xanthomonas campestris* PT1 to suppress or kill the weedy grass.

(2) Prior Art

Bacteria infect grasses causing the grasses to be suppressed or killed. These infections have been known in other parts of the world as important problems for the maintenance of desirable grasses. This method of biological control eliminates the need for herbicides which are relatively toxic chemicals to people and the environment.

A bacterial infection of Toronto creeping bentgrass which is used on golf putting greens is described by Roberts, D. L., et al. in Plant Disease 65, 1014–1015 (1981); Roberts, K. D., et al., Plant Disease 66, 804–806 (1982); Roberts, D. L., et al., Scanning Electron Microscopy IV, 1719–1722 (1983). The bacterium was identified as a *Xanthomonas campestris* by Roberts, D. L. in Phytopathology 73, 810 and 74, 813 (1984). The solution to the problem was treatment of the infection with oxytetracycline, an antibiotic. A disease of *Poa annua* L. was also described by Roberts, D. L. in Phytopathology 75 1289 (1985). U.S. Pat. No. 5,077,045 describes using a strain of Xanthomonas to control *Poa annua*.

The diseases caused by *Xanthomonas campestris* pathovars have also been studied by others and have been found to be selectively pathogenic to particular grass species. Elgi, T., et al. Phytopath Z. 82, 111–121 (1975) first characterized a bacterial infection of cut grasses. Other publications include: Wilkins, P. W., et al. Plant Path 26, 99 (1977); DeCleene, M., et al., Parasitica 37(1) 29–34 (1981); Leyns, F., et al., Parasitica 37, 131–133 (1981); Van Den Mooter, M. et al., Med Fac Landbouww Rijksuniv. Gent 46/3, 787–792 (1981); Van Den Mooter, M., et al Parasitica 37 (1):23–28 (1981); Proc. Fifth Int. Conf. Path Bact, Calif. 332–333 (1981); Egli, T. et al. Phytopath Z. 104, 138–150 (1982); and Leyns et al. Med. Fac. Landbouww Rijksuniv Gent. 47/3 1079–1081 (1982).

OBJECTS

It is, therefore, an object of the present invention to provide a method and composition for biological control of *Poa trivialis* using a *Xanthomonas campestris* pathovar which selectively infects and suppresses or kills the weedy grass by causing a wilt disease. Further, it is an object of the present invention to provide a method which is economical and eliminates the risk from toxic chemicals.

These and other objects will become increasingly apparent by reference to the following description.

DETAILED DESCRIPTION OF THE PREFERRED EMBODIMENTS

The present invention relates to a method for controlling *Poa trivialis* growing with a non-weedy grass which comprises applying an effective amount of a *Xanthomonas campestris* pathovar having the identifying fermentation characteristics of PT1 to the *Poa trivialis* and the non-weedy grass whereby the *Poa trivialis* is suppressed or killed without suppressing or killing the non-weedy grass and wherein the non-weedy grass replaces the *Poa trivialis*.

The present invention also relates to a bacterial concentrate which comprises: a *Xanthomonas campestris* pathovar for *Poa trivialis* having the identifying fermentation characteristics of PT1 which selectively infects and suppresses or kills the *Poa trivialis*; and a preservation agent which preserves the viability of the strain upon storage.

Finally, the present invention relates to a biologically pure culture of a *Xanthomonas campestris* pathovar having the identifying fermentation characteristics of PT1 and which infects and suppresses or kills *Poa trivialis*.

The preferred strain of *Xanthomonas campestris* is at Michigan State University and deposited as PT1. It is freely available to those who request it by name and number. It is being deposited with the ATCC, Manassas, VA as ATCC PTA-182 on Jun. 7, 1999.

The *Xanthomonas campestris* can be applied as an aqueous solution or on an inert carrier. The solution or carrier preferably contains between about $10^3$ and $10^8$ cells per gram (or ml for a solution); for reasons of economics and certainty of infection. It will be appreciated that larger or smaller numbers of the cells per gram or ml can be used so long as infection and suppression of the weedy grass is achieved.

Preferably, the *Xanthomonas campestris* are provided for shipment to users in the form of a concentrate containing at least about $10^6$ cells per gram or ml usually about $10^9$ per ml which can be lyophilized to a greater concentration mixed with a preservative agent, the exact composition of which depends upon the method of the preservation. The cells can be frozen or lyophilized. Where the cells are frozen, glycerol or various sugars and fresh growth media can be used as preservation agents. Amounts usually between 5 and 50% by volume of the glycerol or sugars can be used. Where the cells are lyophilized, nutrient media and/or milk solids can be used for preservation. Generally, the *Xanthomonas campestris* cells are grown to about $10^9$ cells per ml and may then be centrifuged or otherwise concentrated by removal of growth media. They can then be frozen or lyophilized. The lyophilized bacteria can be mixed with an inorganic solid carrier such as clays, talc, inert organic material or the like which may be dusted on the grass or mixed with water and sprayed on the grass.

The *Xanthomonas campestris* pathovars can also be applied using dried infected grass where the grass is used as a nutrient medium to grow and store the bacteria. All of these variations for storing, growing and applying the *Xanthomonas campestris* cultures will be obvious to those skilled in the art.

Generally, a biologically pure culture of the *Xanthomonas campestris* is used for the application to the weedy grass. There is no reason to have other bacteria competing to infect the plant, particularly other *Xanthomonas campestris* which do not suppress or kill the weedy grass and which might infect non-weed grass.

EXAMPLE 1

In this experiment, a frozen culture of *Xanthomonas campestris* pathovar PT1 was used. The *Xanthomonas campestris* culture had been grown in nutrient broth, centrifuged and mixed with equal volumes of glycerol and nutrient medium before freezing. The nutrient medium was Nutrient Broth (Difco Corp., Detroit, MI) or a specialized Xanthomonas growth medium. The thawed culture was inoculated into nutrient medium, grown to about $10^9$ colony forming units (CFU) per ml, centrifuged and then re-suspended in tap water at a concentration of about $10^6$ CFU (colony forming units) per ml.

*Poa trivialis* is a common contaminant in seed lots. It is important to eliminate *P. trivialis* from seed fields to prevent this problem. However, once *P. trivialis* is established in a desirable turfgrass stand, it is nearly impossible to selectively eradicate.

*P. trivialis* can be used as a temporary, desirable turfgrass species particularly in regions of the world, especially southern United States, where Bermuda grass goes dormant. However, it is desirable to quickly eliminate the *P. trivialis* in the spring of the year to allow a smooth transition back to the desirable Bermuda grass. A field study was performed and *P. trivialis* was stressed by treatment with Xanthomonas PT1. This organism caused typical wilt symptoms in *P. trivialis* that were similar to those seen in creeping bentgrass infected with *Xanthomonas campestris* (bacterial wilt).

Example 1 investigates the use of a bacterium, *Xanthomonas campestris*, and it's ability to selectively control *Poa trivialis*, a common weed contaminant of creeping bentgrass seed stock. This study was conducted on a *Poa annua* stand at the Hancock Turfgrass Research Center. Three inch diameter plugs of *Poa trivialis* were transplanted into the study area with 2 plugs placed in each plot. Eight replications of each treatment were made in a randomized block design. Plots were mowed at ½" on a daily (5 days per week) basis just before treatments were applied, and fertility was maintained at ½ lb. nitrogen per 1000 sq. ft. per month. Treatments were applied using a nitrogen backpack sprayer with a single nozzle boom at a rate of 48 gal/acre. Treatments began on Jun. 12, 1996 and were continued according to the schedule below. The following is a list of treatments, rates and application intervals used in this study.

| Treatments | Rate | Application Interval |
|---|---|---|
| 1. Xanthomonas sp. | $5 \times 10^8 CFU/cm^2$ (48 gal per acre) | Daily (5x/week) |
| 2. Autoclaved broth | Volume as above | Daily (5x/week) |
| 3. Mycoshield (a) | 2.5#/1000 ft$^2$ | 14 days |
| 4. Untreated control | — | — |

(a) contains oxytetracycline calcium complex (equivalent to 11% oxytetracycline–35% total volume).

Data were collected by visually estimating the percentage of each *P. trivialis* plug which was infected with bacterial wilt (See Table 1). The rating taken on Aug. 13, 1996 showed that the daily Xanthomonas treatments gave statistically significant bacterial wilt infection when compared to all 3 of the other treatments. With the advent of delivery systems which can facilitate daily application of biocontrol organisms through the irrigation systems, the feasibility of this Xanthomonas being applied on a daily basis to manage *P. trivialis* is highly likely.

TABLE 1

Visual estimation of percent *Pos trivialis* plugs infected with bacterial wilt (Data collected on August 13, 1996).

| Treatment | Rep 1 | Rep 2 | Rep 3 | Rep 4 | Rep 5 | Rep 6 | Rep 7 | Rep 8 | Mean* |
|---|---|---|---|---|---|---|---|---|---|
| Tetracycline Control | 0 | 0 | 0 | 0 | 0 | 0 | 0 | 5 | 0.6 A |
| Untreated Control | 0 | 0 | 0 | 5 | 5 | 0 | 0 | 0 | 1.3 A |
| Autoclaved Broth | 5 | 5 | 0 | 10 | 5 | 0 | 5 | 5 | 4.4 A |
| Xanthomonas | 30 | 5 | 10 | 5 | 30 | 10 | 60 | 5 | 19.4 B |

*Means followed by the same letter are not significantly different based on analysis using Tukey's Test at p = 0.05.

As can be seen from the foregoing Example 1, *Xanthomonas campestris* PT1, over time, killed the weedy grass. In mixed plots, this allows non-weed grass to replace the *P. trivlalis* and retard re-growth of the weedy grass. This result can be achieved when grasses on a golf course are sprayed in the manner of Example 1. Preferably the spraying is done under conditions of high humidity just after cutting to insure infection by the *Xanthomonas campestris*.

EXAMPLE 2

Another study was conducted at the Hancock Turfgrass Research Center, with some modifications to Example 1. Under greenhouse conditions, 1'×2' flats of *P. trivialis* were grown. These were transplanted in May, 1997 to a bentgrass area which was irrigated and fertilized with ½ lb. nitrogen per 1000 ft$^2$ per month to maintain acceptable turf quality. Plots measured 2'×4.5'. All turf was hand mowed to ½ inch height of cut. Plots were mowed and immediately inoculated 3 times each week. Treatments began on Jun. 12, 1997, using the same methods and treatments as in Example 1, except that treatments 1 and 2 were applied 3 times per week. Four replications of each treatment were included. Ratings were taken on Jul. 22, Jul. 31 and Aug. 8, 1997. The entire study area was also treated with thiophanate fungicide manufactured by WA Cleary Corporation located in Dayton, NJ chlorothalonil fungicide manufactured by Zeneca located in Wilmington, DE all season long to prevent disease.

As Table 2 indicates, the results from the 1997 field study are encouraging.

Quality Ratings of *P. trivialis* Following Inoculation with *Xanthomonas campestris* PT1

TABLE 2

| | | | 1997 | | | |
|---|---|---|---|---|---|---|
| Treatment | Rate | Application Interval | Mean 7/22* | 7/31* | 8/8* |
| Xanthomonas | $10^7$ CFU/cm$^2$ | 3 ×/week | 5.5 A | 4.5 A | 4.5 A |
| Autoclaved Broth | vol. as above | 3 ×/week | 6.5 AB | 6.0 AB | 6.5 AB |
| Untreated Control | — | — | 7.5 BC | 6.5 AB | 7.0 AB |
| Tetracycline | 2.5#/ 1000 ft$^2$ | 14 days | 8.0 C | 8.0 B | 8.3 B |

(Rating scale: 0 (dead)–9 (perfect)
*Treatment means followed by the same letter are not significantly different from each other based on Tukey's Test at p = 0.05.

The *P. trivialis* plots protected with oxytetracycline, and the surrounding creeping bentgrass, looked good all season long. The other plots, especially the ones treated with *Xanthomonas campestris*, showed wilt disease and a decline in quality.

Thus, the present invention provides a means for controlling *Poa trivialis*. This is particularly important in seed fields, lawns, fairways, and greens on golf courses to remove infestations of weedy grass.

The *Xanthomonas campestris* is repeatedly applied to the turfgrass to eliminate the *Poa trivialis*. The application can be as a spray through a watering system on a golf course, sod farm, seed production field, or a lawn.

It is intended that the foregoing Examples be only illustrative and that the present invention be limited only by the hereinafter appended claims.

We claim:

1. A method for controlling *Poa trivialis* growing with a non-weedy grass which comprises applying an effective amount of a *Xanthomonas campestris* pathovar having all of the identifying fermentation characteristics of PT1 deposited as ATCC PTA-182 to the *Poa trivialis* and the non-weedy grass whereby the *Poa trivialis* is suppressed or killed without suppressing or killing the non-weedy grass, wherein the *Xanthomonas campestris* pathovar produces in the method wilt symptoms in the *Poa trivalis* and wherein the non-weedy grass replaces the *Poa trivialis*.

2. The method of claim 1 wherein the *Xanthomonas campestris* pathovar is PTA-182.

3. The method of claim 1 wherein an aqueous solution of the *Xanthomonas campestris* pathovar containing between about $10^3$ and $10^8$ cells per ml is applied to the grass.

4. The method of claim 1 wherein the *Xanthomonas campestris* pathovar is a bacterial concentrate which comprises:
   (a) the *Xanthomonas campestris* pathovar; and
   (b) a stabilizing agent which preserves the viability of the strain upon storage.

5. The method of claim 4 wherein the stabilizing agent is glycerol in an amount between about 5 and 50 percent by volume of the concentrate and wherein the concentrate is refrigerated or frozen.

6. The method of claim 4 wherein the stabilizing agent is a nutrient medium for the *Xanthomonas campestris* pathovar and the concentrate is lyophilized.

7. The method of claim 1 wherein the *Xanthomas campestris* pathovar is dried in diseased grass in which the specific *Xanthomonas campestris* pathovar has been grown.

8. The method of claim 1 wherein the *Xanthomonas campestris* pathovar is mixed with an inert solid carrier for applying the bacterial culture to the grass.

9. The method of claim 1 wherein the *Xanthomonas campestris* pathovar is applied repeatedly to the grass to eliminate the *Poa trivialis* from the non-weed grass.

10. The method of claim 1 wherein the *Xanthomonas campestris* pathovar is applied to the non-weed grass as a spray.

11. The method of claim 1 wherein the *Xanthomonas campestris* pathovar is applied through a watering system for the grass.

12. The method of claim 11 wherein the watering system is on a golf course, sod farm, seed production field, or lawn.

* * * * *